(12) United States Patent
Pande et al.

(10) Patent No.: US 10,758,185 B2
(45) Date of Patent: Sep. 1, 2020

(54) HEART RATE ESTIMATION APPARATUS USING DIGITAL AUTOMATIC GAIN CONTROL

(71) Applicant: Texas Instruments Incorporated, Dallas, TX (US)

(72) Inventors: Tarkesh Pande, Richardson, TX (US); David Patrick Magee, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 563 days.

(21) Appl. No.: 15/203,859

(22) Filed: Jul. 7, 2016

(65) Prior Publication Data

US 2017/0143274 A1 May 25, 2017

Related U.S. Application Data

(60) Provisional application No. 62/260,041, filed on Nov. 25, 2015.

(51) Int. Cl.
*A61B 5/024* (2006.01)
*A61B 5/00* (2006.01)

(52) U.S. Cl.
CPC ........ *A61B 5/7207* (2013.01); *A61B 5/02433* (2013.01); *A61B 5/6824* (2013.01); *A61B 5/6826* (2013.01); *A61B 5/725* (2013.01); *A61B 5/7225* (2013.01); *A61B 5/7257* (2013.01)

(58) Field of Classification Search
CPC . A61B 5/7207; A61B 5/02433; A61B 5/6824; A61B 5/7225; A61B 5/725; A61B 5/7257
See application file for complete search history.

(56) References Cited

U.S. PATENT DOCUMENTS 3,972,320 A * 8/1976 Kalman ............... A61B 5/0002
600/519
4,312,358 A 1/1982 Barney
(Continued)

FOREIGN PATENT DOCUMENTS

CN 1531407 A 9/2004
CN 102697492 A 10/2012
(Continued)

OTHER PUBLICATIONS

Jose Epifanio da Franca et al., "Analog-to-Digital Conversion" Wiley Encyclopedia of Electrical and Electronics Engineering, edited by John G. Webster, published 2000 by John Wiley & Sons, Inc.*
(Continued)

*Primary Examiner* — Katherine L Fernandez
*Assistant Examiner* — Colin T. Sakamoto
(74) *Attorney, Agent, or Firm* — Michael A. Davis, Jr.; Charles A. Brill; Frank D. Cimino

(57) ABSTRACT

Disclosed examples include heart rate monitor systems and methods to estimate a patient heart rate, in which a processor filters digital photoplethysmogram (PPG) sample values representing transmission or reflection of a light signal in the patient during a time window, performs motion compensation processing on the filtered values, computes a gain value for individual segments of the time window using the motion compensated values, applies the individual gain values to the motion compensated values of blocks associated with the corresponding segments, and determines a heart rate estimate value representing the patient heart rate according to the frequency content of the adjusted values.

20 Claims, 11 Drawing Sheets

(56) References Cited

U.S. PATENT DOCUMENTS

| | | | |
|---|---|---|---|
| 5,316,008 | A | 5/1994 | Suga et al. |
| 5,730,142 | A | 3/1998 | Sun et al. |
| 5,865,755 | A | 2/1999 | Golub |
| 6,599,251 | B2 | 7/2003 | Chen et al. |
| 6,723,054 | B1 | 4/2004 | Baruch et al. |
| 7,993,275 | B2 | 8/2011 | Banet et al. |
| 2008/0097633 | A1 | 4/2008 | Jochelson et al. |
| 2010/0280402 | A1 | 11/2010 | Dunbar et al. |
| 2011/0293195 | A1* | 12/2011 | Nakagami ............ H04N 19/61 382/233 |
| 2014/0073960 | A1* | 3/2014 | Rodriguez-Llorente .................... A61B 5/7246 600/479 |
| 2014/0114147 | A1* | 4/2014 | Romesburg ........ A61B 5/02416 600/301 |
| 2014/0213863 | A1 | 7/2014 | Loseu et al. |
| 2014/0257049 | A1 | 9/2014 | Soundarapandian et al. |
| 2015/0094552 | A1* | 4/2015 | Golda ................ A61B 5/04325 600/336 |
| 2015/0094592 | A1 | 4/2015 | Ravindran et al. |
| 2015/0112208 | A1 | 4/2015 | He et al. |
| 2015/0196256 | A1* | 7/2015 | Venkatraman .......... A61B 5/721 600/301 |
| 2015/0196257 | A1 | 7/2015 | Yousefi et al. |
| 2015/0313549 | A1 | 11/2015 | Lee et al. |
| 2015/0366469 | A1 | 12/2015 | Harris et al. |
| 2016/0317097 | A1 | 11/2016 | Adams et al. |
| 2016/0324477 | A1 | 11/2016 | Gunturi et al. |
| 2017/0020398 | A1 | 1/2017 | Emadzadeh |
| 2017/0143274 | A1 | 5/2017 | Pande et al. |
| 2017/0367657 | A1 | 12/2017 | Pande et al. |

FOREIGN PATENT DOCUMENTS

| | | |
|---|---|---|
| CN | 102843966 A | 12/2012 |
| CN | 103020472 A | 4/2013 |
| CN | 104462858 A | 3/2015 |
| CN | 105380630 A | 3/2016 |
| JP | 2001340309 A | 12/2001 |
| JP | 2011519653 A | 7/2011 |
| WO | 2005020798 A2 | 3/2005 |

OTHER PUBLICATIONS

Allen et al., "Photoplethysmography and its application in clinical physiological measurement" Physiological Measurement, vol. 28, No. 3, 2007.*

Hertzman, "The Blood Supply of Various Skin Areas as Estimated by the Photoelectric Plethysmograph", Amer. J. Physiol., 1938; 1924: pp. 328-400.

Wijshoff et al., "Reducing Motion Artifacts in Photoplethysmograms by Using Relative Sensor Motion: Phantom Study", J. Biomed. Opt. 17(11), 117007 (Nov. 29, 2012), 16 pgs.

Fukushima et al., "Estimating Heart Rate Using Wrist Type Photoplethysmography and Acceleration Sensor While Running", Engineering in Medicine and Biology Society (EMBS), 2012 Annual Int'l Conf. of the IEEE 2012, pp. 2901-2904.

Zhang, et al., "Troika: A General Framework for Heart Rate Monitoring Using Wrist-Type Photoplethysmographic Signals During Intensive Physical Exercise", IEEE Trans Biomedical Engineering, vol. 62, No. 2, Feb. 2015, 10 pgs.

Schack, et al., "A New Method for Heart Rate Monitoring During Physical Exercise Using Photoplethysmopraphic Signals", European Signal Processing Conf., Sep. 2015 (EUSIPCO 2015), 5 pgs.

Karantonis et al., "Implementation of a Real-Time Human Movement Classifier Using a Triaxial Accelerometer for Ambulatory Monitoring", IEEE Transactions on Information Technology in Biomedicine, vol. 10, No. 1, Jan. 2006, pp. 156-167.

Pande, et al. U.S. Appl. No. 15/237,941, filed Aug. 16, 2016 for "Heart Rate Estimation Apparatus with State Sequence Optimization," 35 pages.

Pande, et al. U.S. Appl. No. 15/192,456, filed Jun. 24, 2016 for "Photoplethysmogram with Motion Artifact Compensation," 17 pages.

International Search Report for PCT/US2016/063780 dated Mar. 6, 2017.

Office Action for Chinese Patent Application No. 201611067402.9, dated Jul. 1, 2020, 6 pages.

Amann, et al., "Detecting Ventricular Fibrillation by Time-Delay Methods," IEEE Transactions on Biomedical Engineering, vol. 54, No. 1, 1, Jan. 2007, pp. 174-177.

Shao, Zhi-Gang,"Network Analysis of Human Heartbeat Dynamics," Applied Physics Letters 96, 073703 (2010), 3 pages.

CN105380630A, Machine Translation, 31 pages.
CN102843966A, Machine Translation, 21 pages.
CN1531407A, Machine Translation, 23 pages.
JP2011519653, Machine Translation, 16 pages.
CN102697492A, Machine Translation, 22 pages.
CN104462858A, Machine Translation, 12 pages.
CN103020472A, Machine Translation, 28 pages.

* cited by examiner

US 10,758,185 B2

HEART RATE ESTIMATION APPARATUS USING DIGITAL AUTOMATIC GAIN CONTROL

Under 35 U.S.C. § 119, this application claims priority to, and the benefit of, U.S. Provisional Patent Application Ser. No. 62/260,041 that was filed on Nov. 25, 2015 and is entitled "IMPROVING PERFORMANCE IN HEART RATE ESTIMATION USING A dAGC", the entirety of which is incorporated by reference herein.

BACKGROUND

A photoplethysmogram ("PPG") is an optically obtained volumetric measurement of an organ (an optical plethysmogram). Photoplethysmography can be used in wearable activity monitors, medical equipment or other systems to optically detect blood volume changes in blood vessels to monitor blood flow, blood content, respiration rate and other circulatory conditions, where the intensity of back scattered light correlates to the amount of blood volume. PPG signals can be obtained in a number of different ways, including assessing absorption of light transmitted through, or reflected from, a patient's skin. A light source at a particular wavelength (typically, red, infrared or green) directs light toward the patient's skin. A photodiode or other optical sensor generates the PPG signal indicating the measured light absorption (transmission) or reflection, and changes in the PPG signal can be used to detect the pulse rate of the patient's heart. PPG based heart rate estimation during motion is difficult, as motion artifacts show up in the PPG signal. The motion artifacts are caused due to hemodynamic effects, tissue deformation, and sensor movement relative to the skin. Motion compensation techniques have been proposed to remove the motion component in the PPG signal using information from an external sensor reference, such as an accelerometer. Some approaches use spectrum subtraction to first remove the spectrum of the acceleration data from that of the PPG signal prior to heart rate estimation. Another motion compensation approach uses compressed sensing techniques combined with signal decomposition for de-noising and spectral tracking. The PPG signal fidelity can be further improved using normalized least means squares (NLMS) and non-coherent combination in the frequency domain.

SUMMARY

Disclosed examples include heart rate monitor systems and methods to estimate a patient's heart rate. PPG sample values representing transmission or reflection of a light signal in the patient during a time window are filtered and motion compensated. A gain value is computed for individual segments of the time window using the motion compensated values, and the gain values are applied to the motion compensated values associated with the corresponding segments. A heart rate estimate value representing the patient heart rate is determined according to the frequency content of the adjusted values.

DETAILED DESCRIPTION

Figure 1:
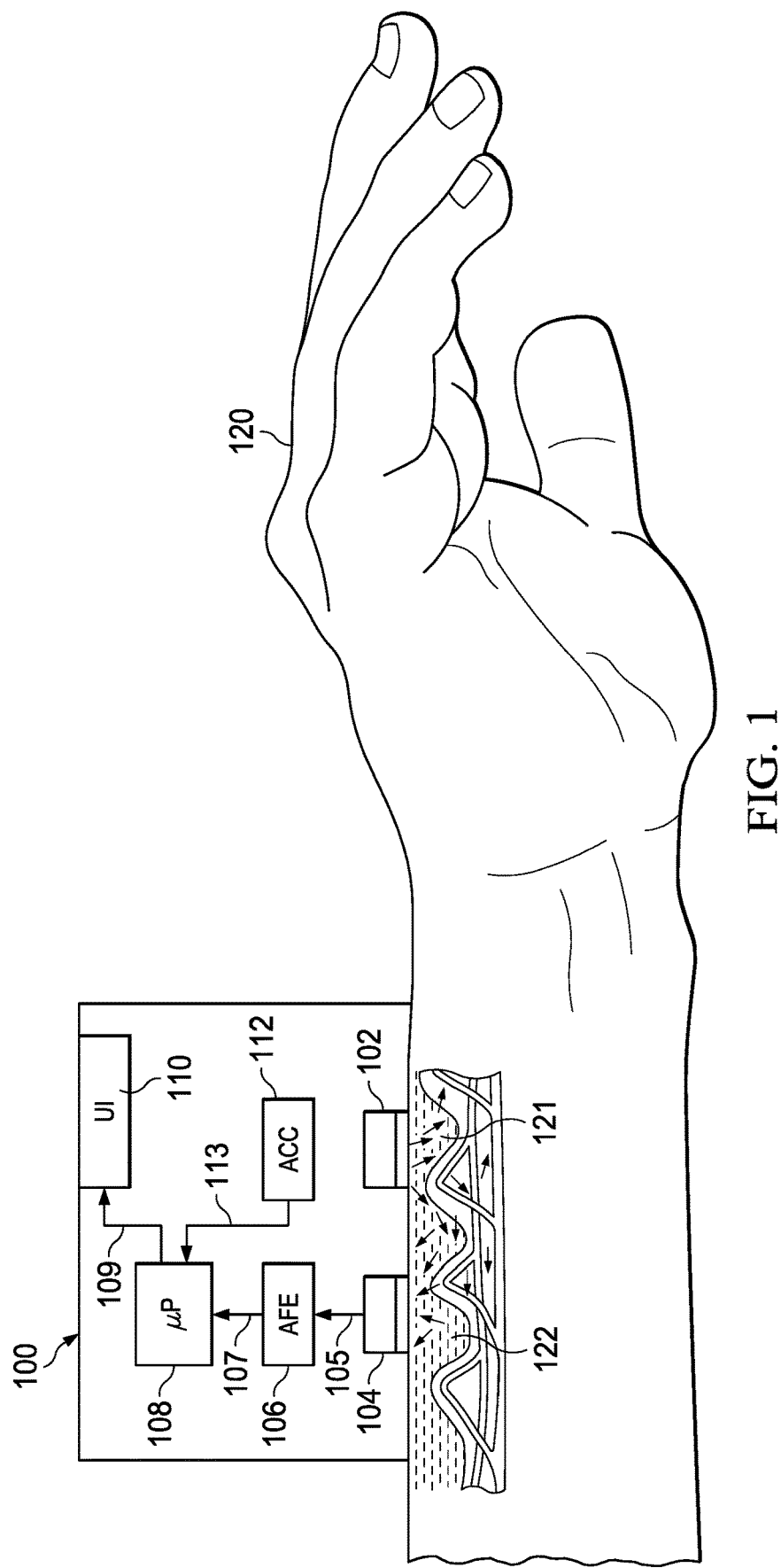
FIG. 1 is a partial schematic diagram of a system to measure reflected light from a patient's skin for estimating the patient heart rate.

In the drawings, like reference numerals refer to like elements throughout, and the various features are not necessarily drawn to scale. In the following discussion and in the claims, the terms "including", "includes", "having", "has", "with", or variants thereof are intended to be inclusive in a manner similar to the term "comprising", and thus should be interpreted to mean "including, but not limited to . . . ."

Figure 2:
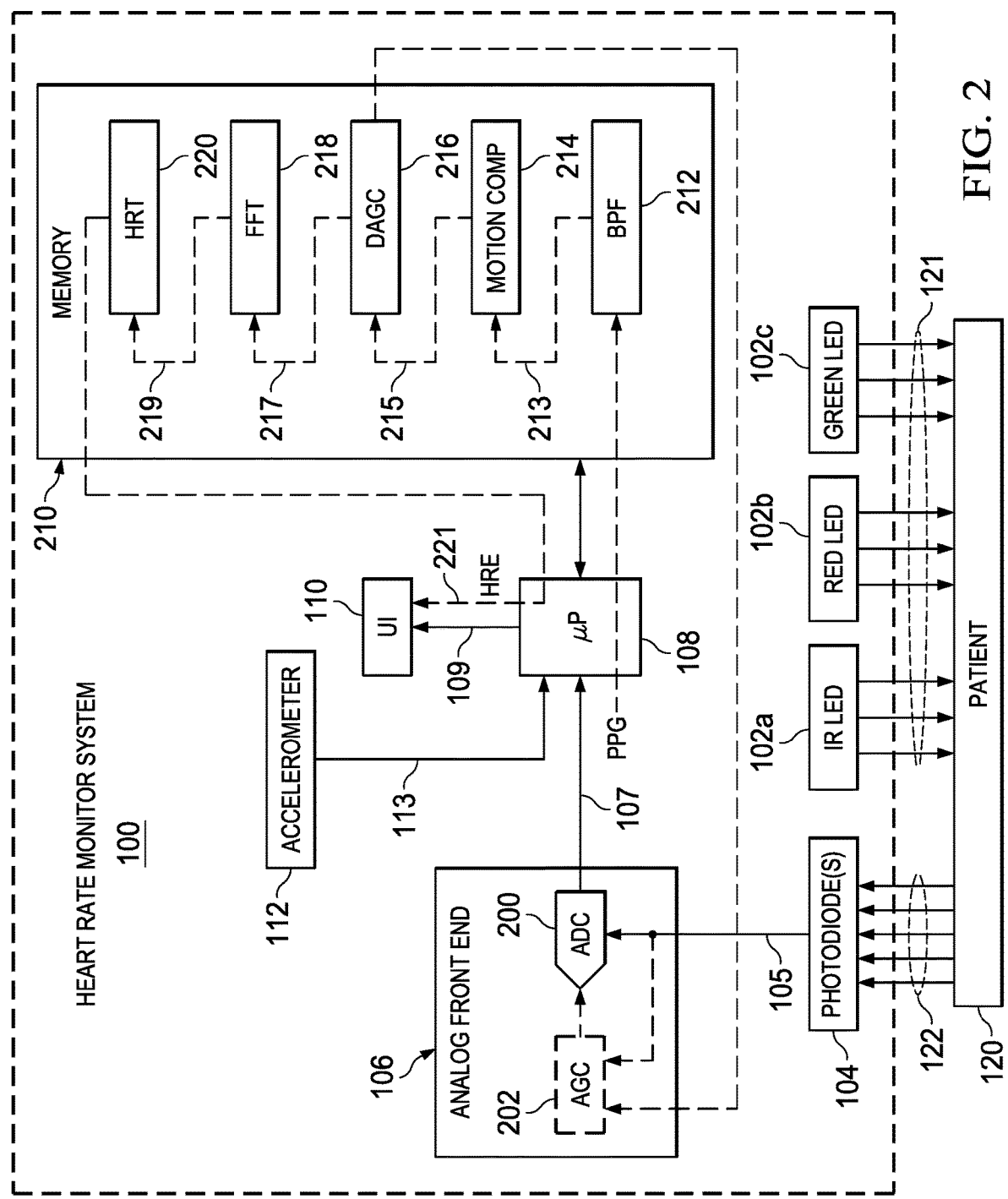
FIG. 2 is a detailed schematic diagram of an example heart rate estimation system using digital automatic gain control after motion compensation and before Fourier transformation.
Figure 3:
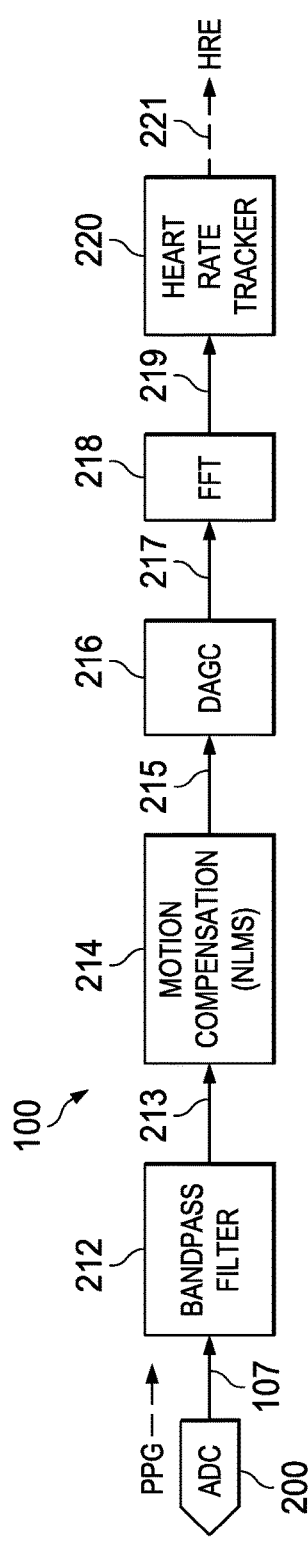
FIG. 3 is a schematic diagram of a heart rate estimation example for processing a single light signal in the system of FIGS. 1 and 2.

Referring initially to FIGS. 1 and 2, FIG. 1 shows a wearable heart rate monitor system 100 to measure reflected light from the skin of a patient 120 to determine a heart rate estimate (HRE) value. FIG. 2 shows further details of the heart rate estimation system 100 using digital automatic gain control (DAGC) following motion compensation processing and prior to frequency analysis. The example system 100 is shown in FIG. 1 adjacent to a patient wrist for reflective PPG monitoring, and uses reflected light measurement techniques with one or more light sources (e.g., LED(s)) 102 and one or more optical sensors (e.g., photo diode(s)) 104. The light source 102 and the optical sensor 104 are disposed along a common plane in this example. Coplanarity of the light source 102 and the sensor 104 is not required in all implementations. In other examples, transmission configurations are possible, with a light source and a light sensor disposed on opposite sides of a patient's finger or other portions of a patient's body to assess light transmission and/or absorption for determining patient heart rate. The light source 102 in FIG. 1 directs a first light signal 121 toward the skin of the patient 120. The first light signal 121 in this example is reflected in the patient 120 with some measure of absorption, and a reflected second light signal 122 is generated. The optical sensor 104 detects the second light signal 122 from the patient 120. In this example, the sensor 104 generates an analog PPG signal 105 that represents reflection of the first light signal 121 in the patient 120. In other examples (not shown) where the sensor 104 and the source 102 are on opposite sides of the patient's finger, the sensor 104 provides a PPG signal 105 that represents transmission or absorption of light through the patient. In one example, a single light source 102 and a single optical sensor 104 are used. The example of FIG. 2 includes multiple LED light sources 102a-102c providing corresponding first light signals 121 at different wavelengths. The first light source 102a in this example provides infrared (IR) light 121, the second source 102b provides red light 121, and the third optical source 121c provides green light 121.

The system 100 further includes an analog front end (AFE) circuit 106. One or more optical sensors 104 receive the second light signal 122, and provide one or PPG signals 105 to the AFE circuit 106. The AFE circuit 106 includes any suitable analog signal conditioning circuitry (not shown) to receive and condition the PPG signal or signals 105, as well as an analog to digital converter (ADC) 200. The ADC 200 samples the PPG signal 105 and generates a plurality of digital PPG sample values 107 in a first time window for use in estimating the patient heart rate corresponding to the time window. Example signals and corresponding first time windows W1 are illustrated and described below in connection with FIGS. 8, 10, 12 and 14-17. The system 100 in one example operates in continuous fashion to continually monitor received PPG signals 105 and to estimate the patient heart rate based on an integer number of samples in individual ones of a series of multiple time windows W to yield a heart rate estimate (HRE) value corresponding to the individual time windows W.

The ADC 200 operates at a fixed or adjustable sample rate, and the time windows in certain examples include a sufficient number of samples to characterize the PPG signal 105 over multiple heartbeats of the patient 120. For example, the length of the time windows W in one example is on the order of 8-10 seconds. As discussed further below, the system 100 partitions the individual time windows W into an integer number of segments S for digital automatic gain control (AGC) in the digital domain, and in certain examples applies computed gain values K2 individual blocks B associated with individual ones of the segments S. The size of the segments S is preferably large enough to include more than one heartbeat of the patient 120, for example, 2 seconds. The segments S in one example are of equal length, but other embodiments can have segments of different lengths. Where used, the gain application blocks B begin and end at or adjacent to a zero crossing of the PPG signal 105, and typically will not strictly align with the corresponding segments S.

The APE circuit 106 in FIG. 2 also includes an analog automatic gain control (AGC) circuit 202 to adjust the gain of the signal 105 converted by the ADC circuit 200. In certain examples, the AGC circuit 202 receives the signal or signals 105 and dynamically adjusts an input buffer amplifier gain to provide a signal for conversion by the ADC circuit 200. In some examples, as discussed further below, the analog AGC circuit 202 may also receive an external control signal or value used to set the gain for conversion of the PPG signal or signals 105 based on digital automatic gain control (DAGC) operation in the digital domain on previously received samples. In addition, the system 100 may include an accelerometer 112 providing a signal 113 to the processor 108.

The ADC circuit 200 provides digital sample values 107 of the PPG signal to a processor 108 circuit and an associated electronic memory 210 for digital processing to estimate the patient heart rate. The processor circuit 108 can be any suitable digital logic circuit, programmable or pre-programmed, such as an ASIC, microprocessor, microcontroller, FPGA, etc. that operates to execute program instructions stored in the electronic memory 210 to implement the features and functions described herein as well as other associated tasks to implement a monitor system 100. In certain examples, moreover, the memory circuit 210 can be included within the processor circuit 108. The processor 108 in the examples of FIGS. 1 and 2 includes an interface connection 109 to a user interface (UI) 110, such as a display (not shown). In certain examples, the memory 103 constitutes a non-transitory computer-readable storage medium that stores computer-executable instructions that, when executed by the processor 108, perform the various features and functions detailed herein.

In the example of FIG. 2, the processor 108 implements instructions corresponding to various functions or components 212-220 in the memory 210, including a filter component (bandpass filter or BPF) 212, a motion compensation component 214, a digital automatic gain control (DAGC) component 216, a Fast Fourier Transform (FFT) component 218 and a heart rate tracker (HRT) component 220. In operation, the processor 108 implements the functional components 220 to operate on the received PPG samples 107 in order to provide a heart rate estimate value (HRE) 221, which can then be provided to the user interface (UI) 110, such as a display to render the HRE value 221 to the patient 120.

The processor 108 implements the filter component 212 in order to filter 706 the digital PPG sample values 107 to generate a plurality of filtered values 213 corresponding to the first time window W1. Low pass filtering can be provided by the component 212 in order to remove certain motion artifacts or other low frequency components not related to the patient heart rate. In the illustrated example, bandpass filtering is provided by processor execution of the component 212 in order to also remove high-frequency noise components. The processor 108 in this example performs motion compensation processing on the filtered values 213 to generate a plurality of motion compensated values 215 corresponding to the first time window W1. In one example, the motion compensation component 214 implements any suitable motion compensation algorithms or processing, including spectrum subtraction, compressed sensing with signal decomposition, and/or normalized least means squared or NLMS processing.

Following motion compensation, the processor 108 provides digital domain automatic gain adjustment or automatic gain control processing by implementing the component 216 on the motion compensated values 215. The gain adjustment processing via the component 216 operates on segments S of the motion compensated data samples for the current time window W, including computation of a gain value $K_i$ corresponding to each individual segment S. In one example, the time window W is 8 seconds, including four segments S1-S4 of 2 seconds each, with each segment S including an integer number N samples. The processor 108 in one example computes four gain values $K_i$ (i=1, 2, 3, 4) individually corresponding to the segments S1-S4 using the motion compensated values 215, in order to promote average power across the segments S1-S4 of the current time window W. The processor 108 in this example applies the individual gain values $K_i$ to the motion compensated values 215 of four blocks B individually associated with the segments S1-S4 to generate a plurality of adjusted values 217 for the corresponding time window W. And one example, the gain values K are applied to the corresponding samples by multiplication. In another example, the processor 108 applies the gain values K to the sampled data using binary bit shifting to generate the adjusted values 217. As discussed further below in connection with FIGS. 16 and 17, at least some of the individual blocks B begin and end at or adjacent to a zero crossing of the motion compensated values 215 in certain examples.

Once the gain adjustment processing has been implemented using the component 216, the processor 108 implements the FFT component 218 and the HRT component 220 in order to determine the heart rate estimate HRE value 221 representing the heart rate of the patient 120 for the time window W according to the frequency content of the adjusted values 217. In one example, the processor computes the frequency content of the adjusted values 217 using a Fast Fourier Transform FFT algorithm via the instructions of the component 218 in order to generate a frequency spectrum including frequency component values 219. The processor 108 implements the heart rate tracking component 220 in this example to determine the HRE value 221 according to a discernible peak in the frequency spectrum data 219.

Figure 4:
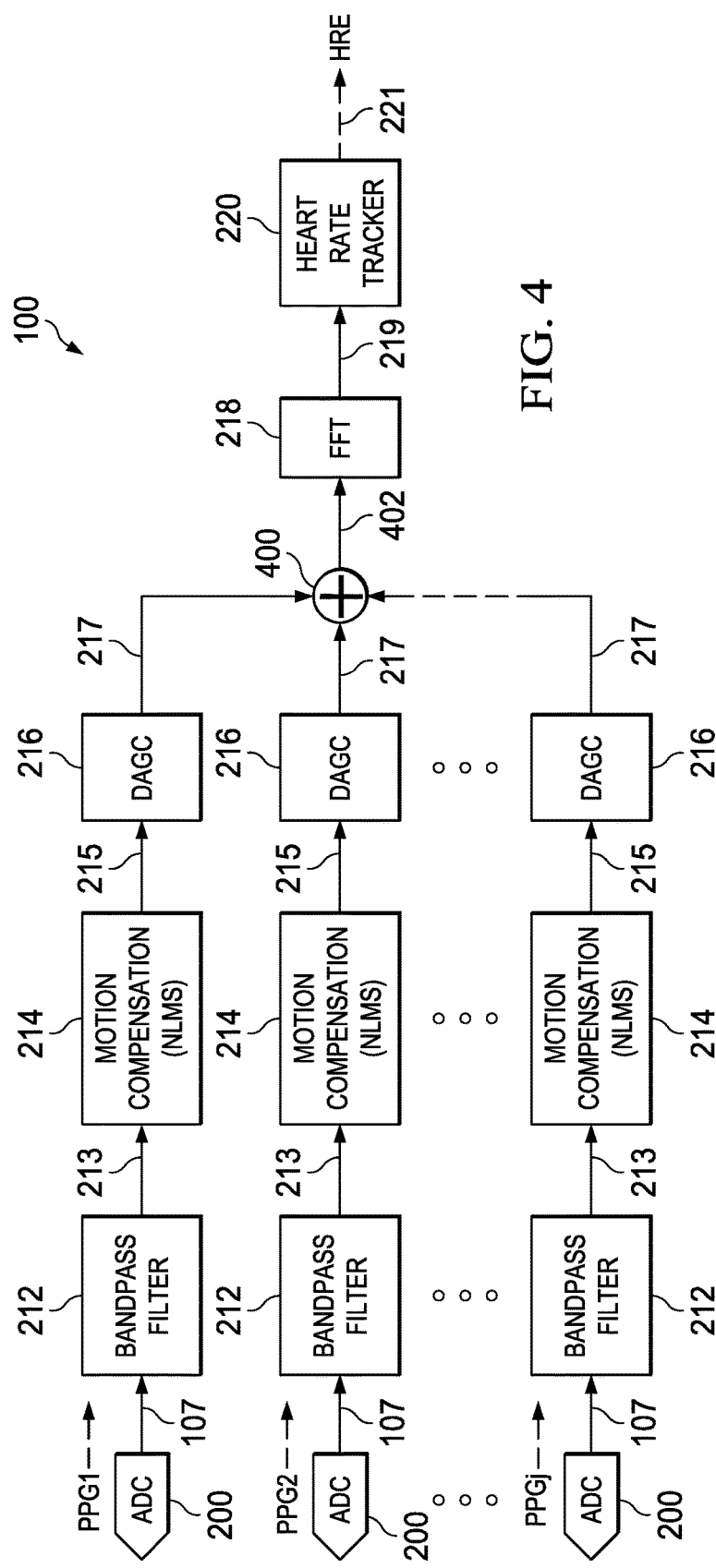
FIG. 4 is a schematic diagram of a multi-channel heart rate estimation example with gain adjusted samples combined before Fourier transformation in the system of FIGS. 1 and 2.

Referring also to FIGS. 3-6, FIG. 3 illustrates the digital domain processing for a single PPG light signal 105 in the system 100 of FIGS. 1 and 2 as described above. In other examples, multiple light signals 105 can be processed using the components 212-220, for example, based on first light signals 121 generated by light sources 102 of different wavelengths (e.g., infrared or IR, red, green, etc.). The system 100 in this example may include a corresponding set of multiple optical sensors (e.g., photodiodes) 104, each receiving a corresponding light signal 122 and generating a corresponding second analog PPG signal 105 representing transmission or reflection in the patient 120. For example, the first optical sensor 104 detects the second light signal 122 representing transmission or reflection of the first light signal 121 from the first light source 102a, and the processor 108 operates on sampled values in a first signal processing chain associated with the first wavelength. For an additional light source 102b and an associated second optical sensor 104, the analog PPG signal 105 corresponds to a detected fourth light signal 122 representing transmission or reflection of a third light signal from the second source 102b, and the processor 108 forms filtering and motion compensation (and possibly gain adjustment) in a second digital signal processing chain. FIG. 4 shows an example of the digital processing in the system 100 with an integer number j digital signal processing channels corresponding to j PPG sample sets PPG1, PPG2, . . . PPGj. In this example, the processor 108 performs filtering, motion compensation and gain adjustment processing via the components 212, 214 and 216 for each of the individual signal channels in the digital domain. The gain adjusted samples 217 are then combined by the processor 108, symbolized by a summation component 400 and FIG. 4 in order to generate a plurality of combined adjusted values 402. The processor 108 then performs FFT processing 218 and heart rate tracking processing 220 to determine the HRE value 221.

Figure 5:
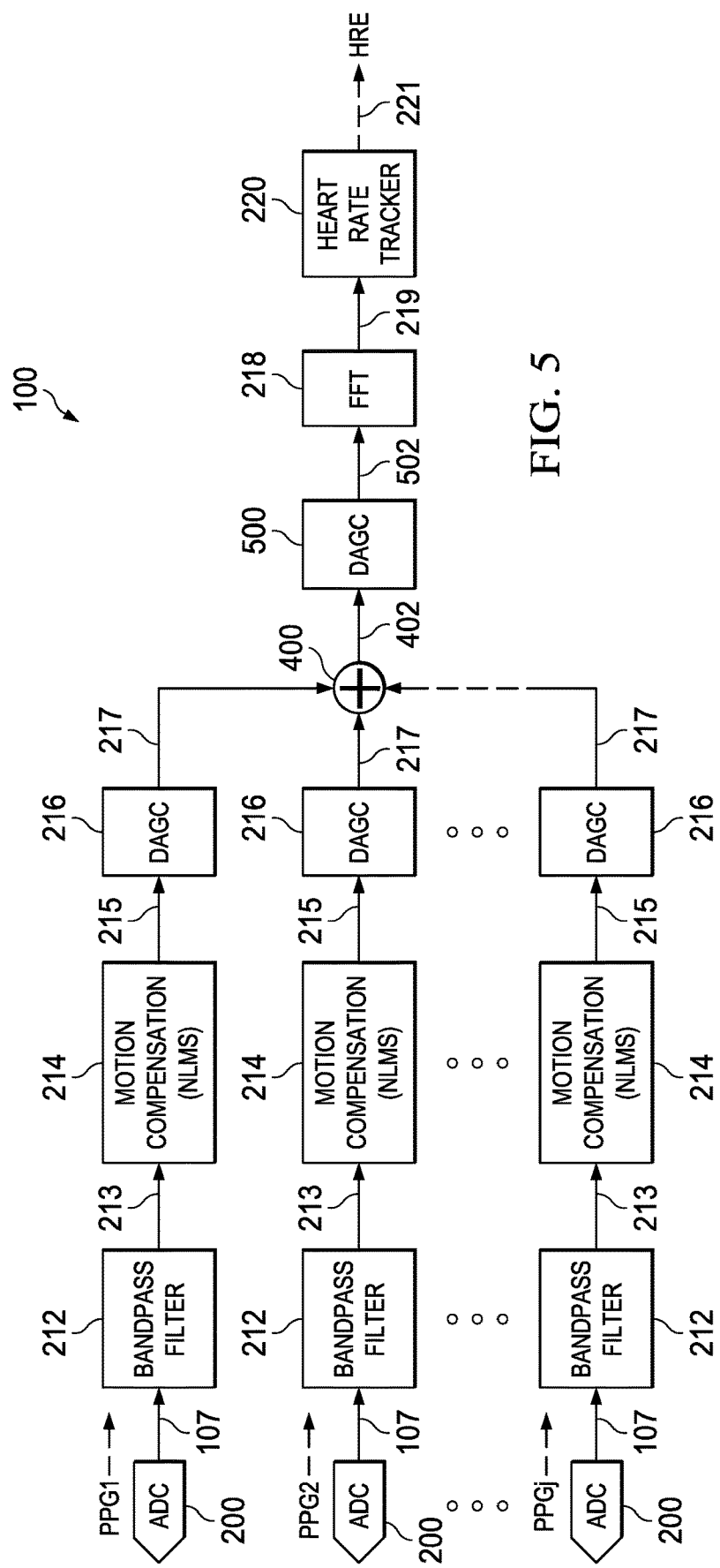
FIG. 5 is a schematic diagram of another multi-channel heart rate estimation example with gain adjusted samples combined and provided for further gain adjustment and Fourier transformation in the system of FIGS. 1 and 2.

Another multiple signal example is shown in FIG. 5, in which the individual signal channel processing includes bandpass filtering 212, motion compensation 214 and digital automatic gain control processing 216. In this case, the processor 108 combines the gain adjusted samples 217 using the summation component 400, and these combined values 402 are provided to a further (e.g., combined) digital automatic gain control component 500. The processor 108 again implements digital gain adjustment via the component 500, in similar fashion to the individual channel gain adjustment processing components 216, in order to compute gain values for individual segments S of the combined data 402, and to apply the individual gain values two blocks associated with the segments S. The resulting combined, gain adjusted values 502 undergo FFT processing 218 in order to generate the frequency spectrum data 219, and the heart rate tracker component 220 determines the HRE value 221 according to the frequency spectrum data 219.

Figure 6:
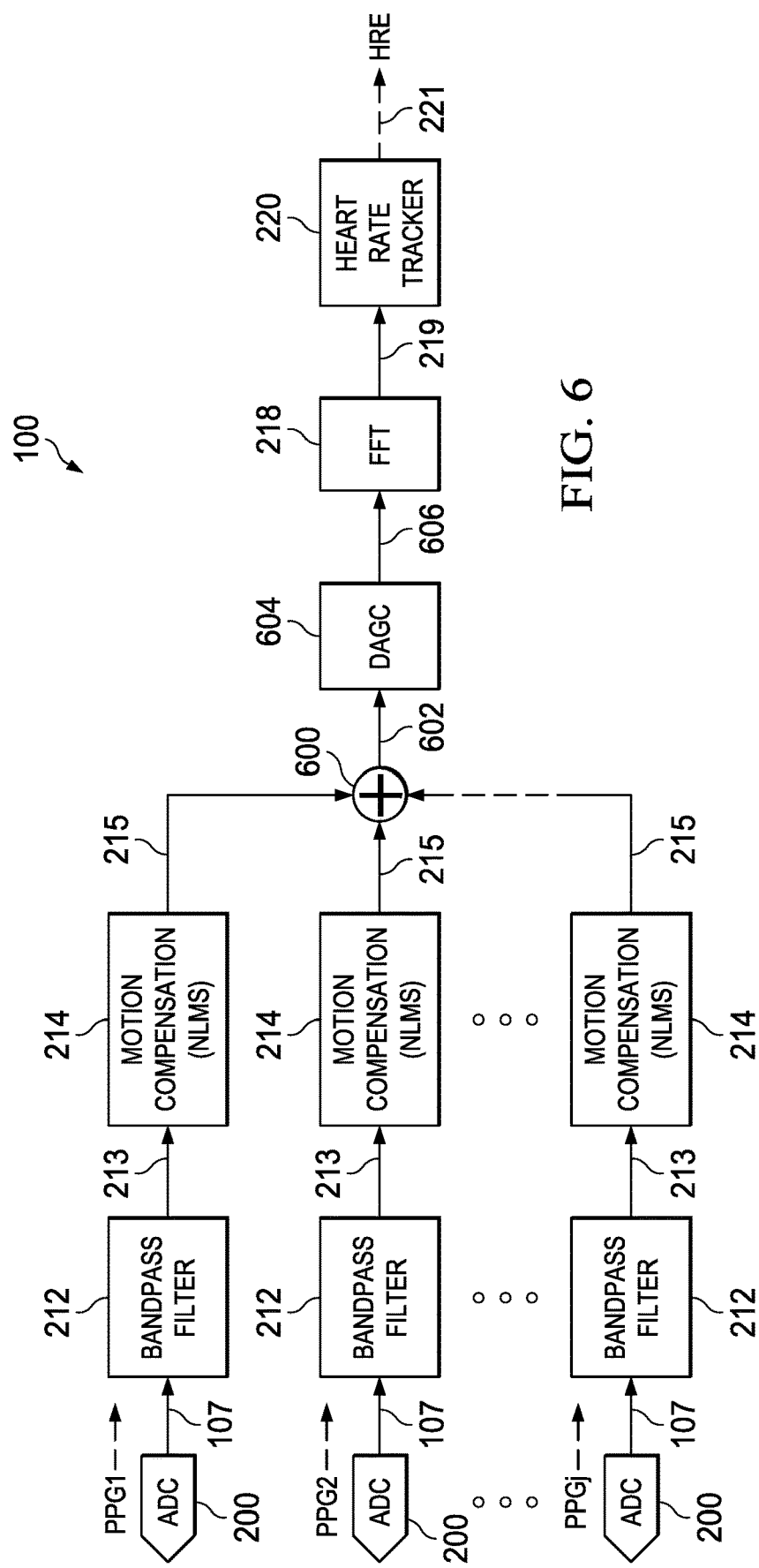
FIG. 6 is a schematic diagram of a further multi-channel heart rate estimation example with motion compensated samples combined for subsequent gain adjustment and Fourier transformation in the system of FIGS. 1 and 2.

FIG. 6 illustrates another multi-channel heart rate estimation example in the system 100. In this case, the individual channel data PPG1, PPG2, . . . , PPGj undergoes filtering and motion compensation processing via the components 212 and 214. The resulting sets of motion compensated values 215 are then combined by a summation component 600 to generate combined motion compensated values 602. The processor 108 performs digital automatic gain compensation processing via a component 604 on the combined motion compensated values 602 to generate gain adjusted value 606. In this example, the processor 108 then generates the frequency spectrum data 219 using the FFT processing 218, and determines the HRE value 221 according to the frequency spectrum data 219 using the HRT component 220.

Figure 7:
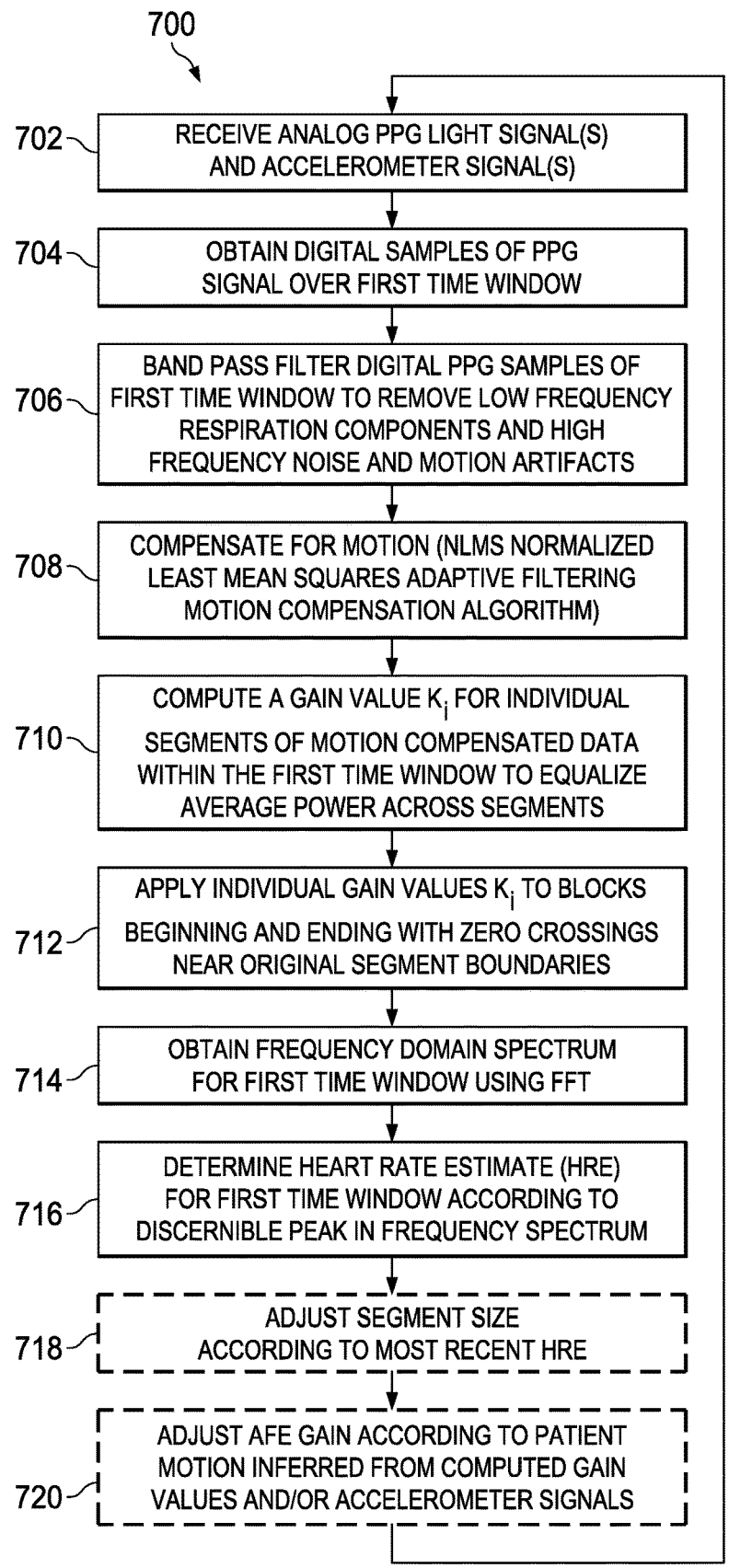
FIG. 7 is a flow diagram of a method to estimate a heart rate of a patient.

FIG. 7 shows the an example process or method 700 to estimate a patient heart rate. The method 700 can be implemented in any suitable processing system in which digital automatic gain control processing for gain adjustment processing is performed on digital samples following motion compensation, and prior to frequency analysis. In one example, the processor 108 of the system 100 is programmed by instructions in the memory 210 in order to implement the method 700. In other implementations, the process 700 can be implemented in a general purpose computer (not shown), in a medical equipment processor, or other processing circuit or system. At 702 in FIG. 7, one or more analog light signals are received. In certain examples, accelerometer signals can be received at 702. At 704, digital samples are obtained of the analog PPG signal over a corresponding first time window W, for example, using an ADC circuit 200 as described above. At 706, the digital PPG samples of the window W are filtered, for example, by execution of digital filtering program instructions 212 by the processor 108 described above. At 708, the filtered samples are compensated for motion. In one example, the motion compensation at 708 is implemented using NLMS adaptive filtering or other suitable algorithm by processor execution of the compensation component instructions 214 above.

The method 700 further includes gain adjustment processing at 710 and 712, including computing a gain value at 710 for individual segments of the motion compensated data within the time window to promote equalization of average power across the segments. The individual gain values are applied to blocks beginning and ending with a zero crossing is near the original segment boundaries. At 714, frequency domain spectrum data is computed or otherwise obtained for the first time window using FFT or other suitable frequency analysis processing. A heart rate estimate value (HRE) is then determined at 716 for the time window according to a discernible peak in the frequency spectrum data.

In certain implementations, the method 700 further includes adjusting the segment size according to a most recent HRE value 221. For example, a newly determined HRE value 221 can indicate a relatively low heart rate for the patient 120. In this case, the processor 108 in the system 100 can automatically increase the segment size at 718 in FIG. 7 in order to enhance the number of samples obtained for each heartbeat. In another case, the most recently determined HRE value 221 can indicate a very high heart rate, in which case the processor 108 can reduce the segment size at 718 so that, for example, only one or two heart rate cycles are in the segment so that the FFT can do a better job to estimate the average heart rate.

In certain examples, the process 700 further includes adjusting an analog gain control circuit at 720 (e.g., AGC 202 coupled with the ADC 200 in FIG. 2) at least partially according to the computed gain values $K_i$ for the individual segments S corresponding to the time window W. In this manner, the processor 108 uses the information obtained during the digital gain adjustment processing 216 in order to feedback a gain adjustment control to the ABE circuit 106.

FIGS. 8-15 illustrate example PPG waveforms and signals to illustrate operation of the system 100 and processing according to the method 700 described above. Digital automatic gain control (DAGC) prior to FFT processing provides certain advantages in assessing heart rate based on PPG signals. This signal processing order is in contrast to communications based digital signal processing, in which any digital gain control processing is typically performed immediately after analog to digital conversion, and before any further signal processing in order to maximize signal bit resolution. In heart rate spectral peak estimation and tracking, performance improvements are obtained if the DAGC is placed after the motion compensation algorithms (e.g., NLMS) and prior to FFT as in the above-described system 100 and method 700. In heart rate monitoring systems, when the patient is at rest (e.g., no motion) the PPG signal can be assessed by simply counting zero crossings, peaks or valleys in order to determine the heart rate.

Patient motion can introduce additive and/or multiplicative motion artifacts, which appear in the PPG signal. For example, if the optical heart rate system 100 is loose on the patient 120, and moves relative to the patient's skin when the patient 120 is in motion, the motion artifact effect on the PPG signal is multiplicative. Motion by the patient can cause additive motion artifacts to appear in the PPG signal in cases where the sensor system 100 is firmly mounted to the patient 120. Additive components result in new peaks in the spectral signature while the multiplicative effects result in spectral spreading of the heart rate signature i.e., presence of new peaks (multiplication in the time domain is convolution in the frequency domain). As shown in FIGS. 8-15, the system 100 and method 700 can be advantageously employed to enhance the accuracy of the heart rate estimate value 221.

Figure 8:
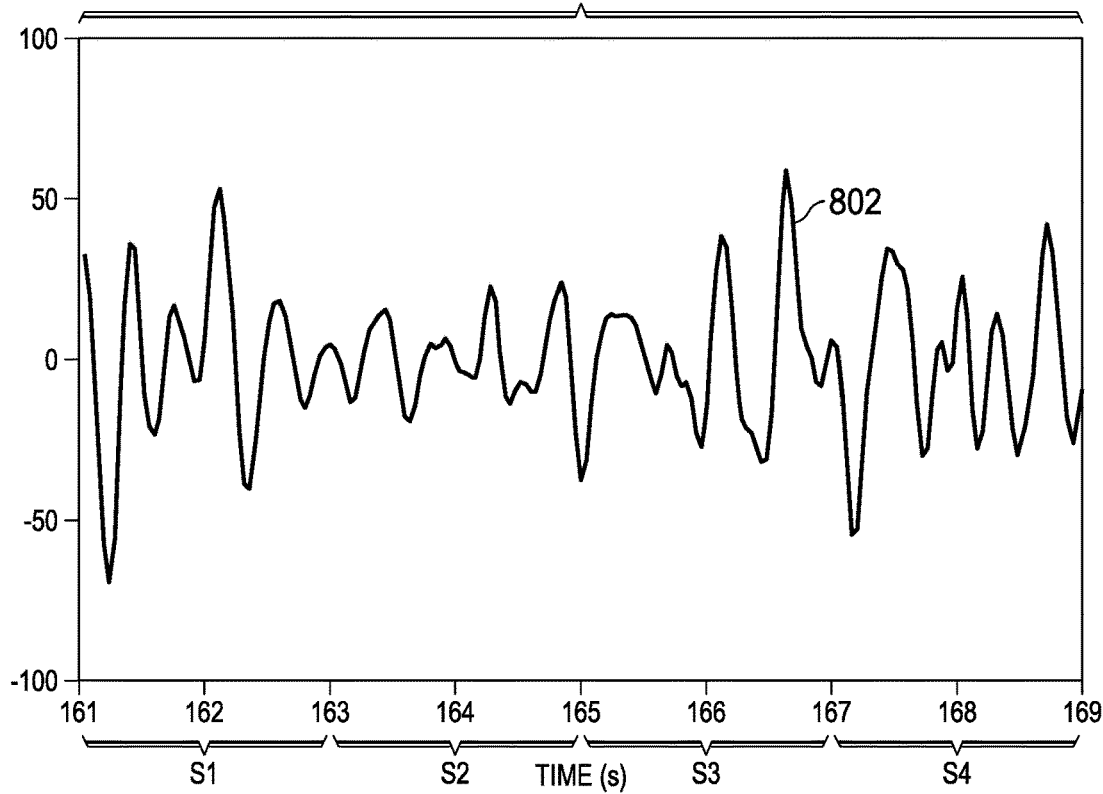
FIG. 8 is a diagram of a PPG signal including motion artifacts.
Figure 9:
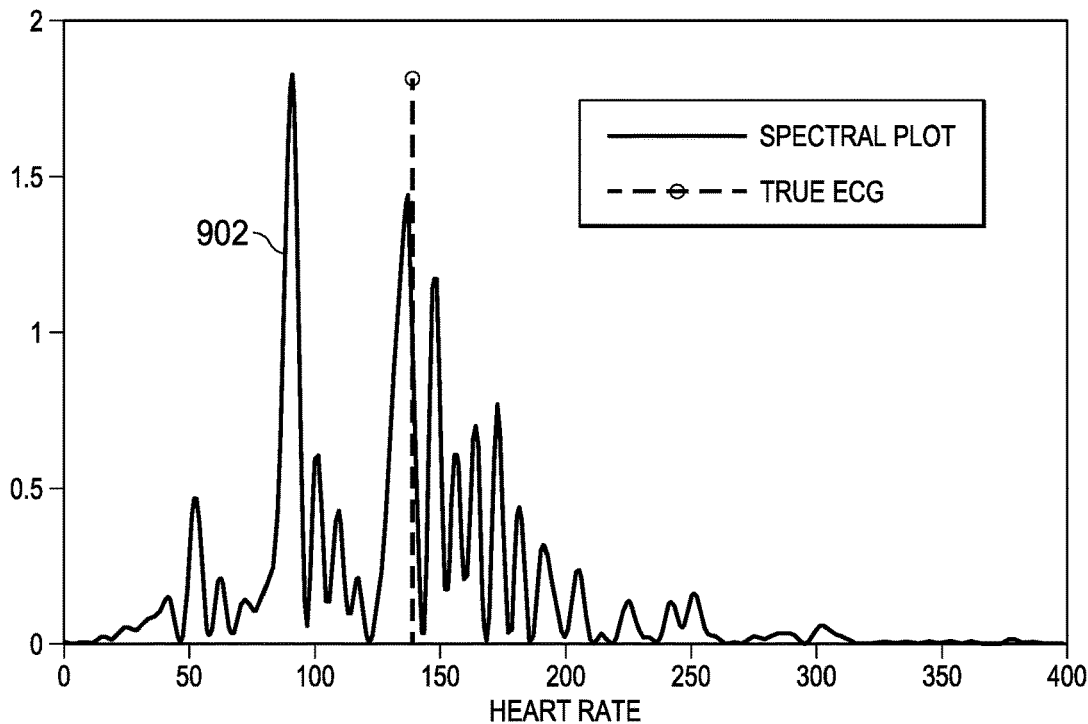
FIG. 9 is a diagram of a frequency spectrum of the PPG signal of FIG. 8 showing a peak value that does not represent the actual patient heart rate.
Figure 10:
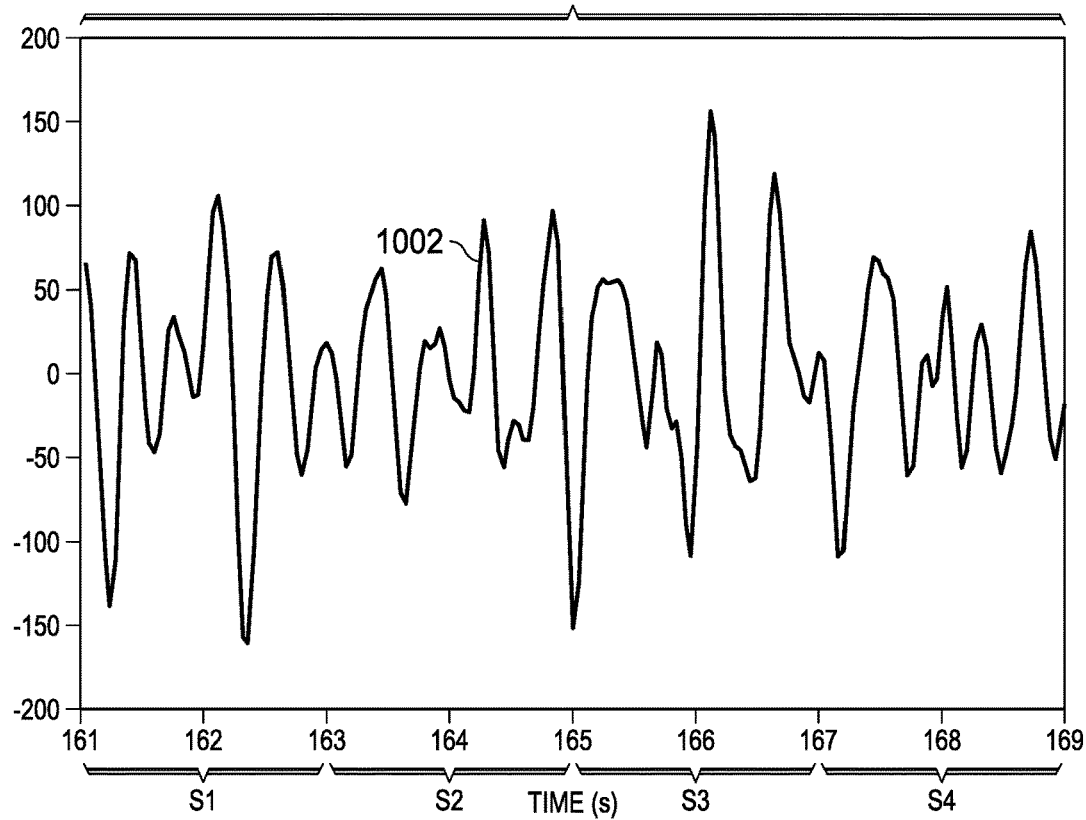
FIG. 10 is a diagram of a gain adjusted signal obtained by digital automatic gain adjustment of the PPG signal of FIG. 8.
Figure 11:
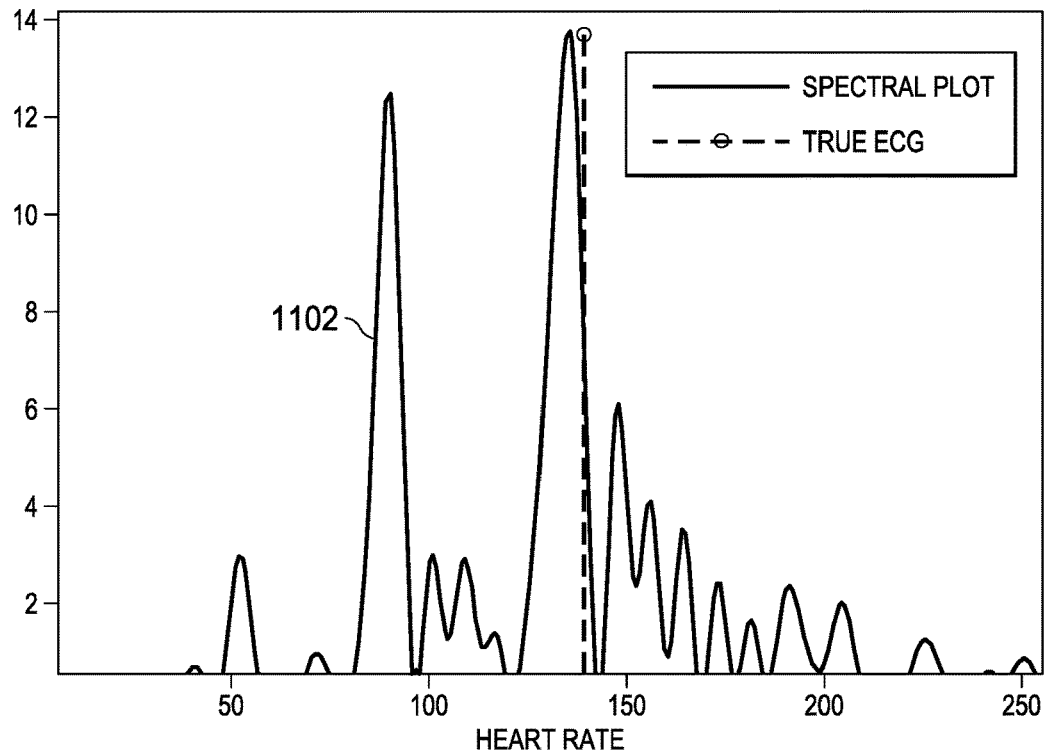
FIG. 11 is a diagram of a frequency spectrum of the gain adjusted signal of FIG. 10 showing a peak value near the actual patient heart rate.

FIG. 8 is a graph including a PPG signal waveform 802 after motion compensation processing over a first time window W1 having a length of 8 seconds. The waveform 802 represents an integer number digital samples, although the curve 802 appears continuous in the drawing. The time window W1 is divided into four segments S1-S4 of 2 seconds each. The PPG signal 802 in this example includes segments S1 and S3 in which the signal amplitude is substantially larger than in the other segments S2 and S4. A graph 900 and FIG. 9 shows a frequency spectrum 902 corresponding to the PPG signal 802 of FIG. 8. As seen in FIG. 9, the highest peak in the frequency spectrum 902 is below 100 beats per minute (bpm), whereas the true heart rate obtained in this example through ECG is at a much higher rate of approximately 140 bpm. A graph 1000 in FIG. 10 shows a gain adjusted waveform 1002 representing gain compensation via the DAGC component 216 using segment gain values $K_1$, $K_2$, $K_3$ and $K_4$ computed to promote average power across the plurality of segments S1-S4 in the time window W1. FIG. 11 provides a graph 1100 showing a frequency spectrum 1102 corresponding to the gain adjusted samples of FIG. 10. The spectrum 1102 in FIG. 11 includes a highest peak generally corresponding to the true patient heart rate, and the local maxima at approximately 90 bpm has been reduced. As seen in FIGS. 8-11, the digital domain gain adjustment advantageously improves the accuracy of the heart rate estimation system 100.

Figure 12:
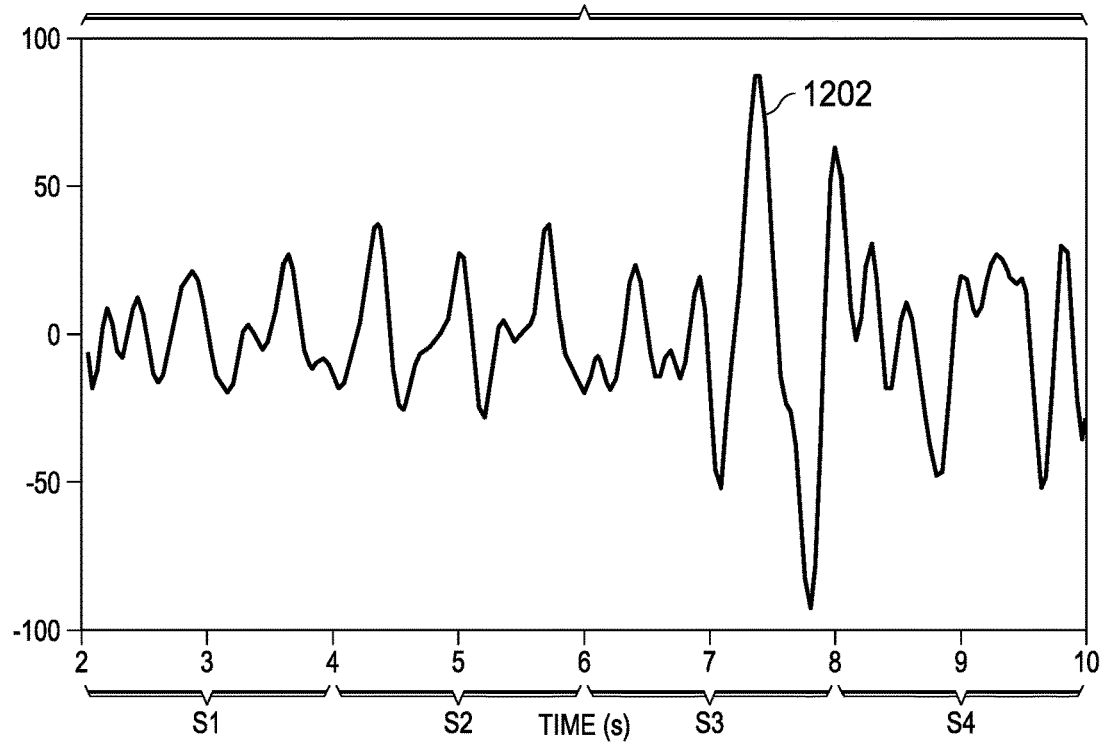
FIG. 12 is a diagram of another example PPG signal.
Figure 13:
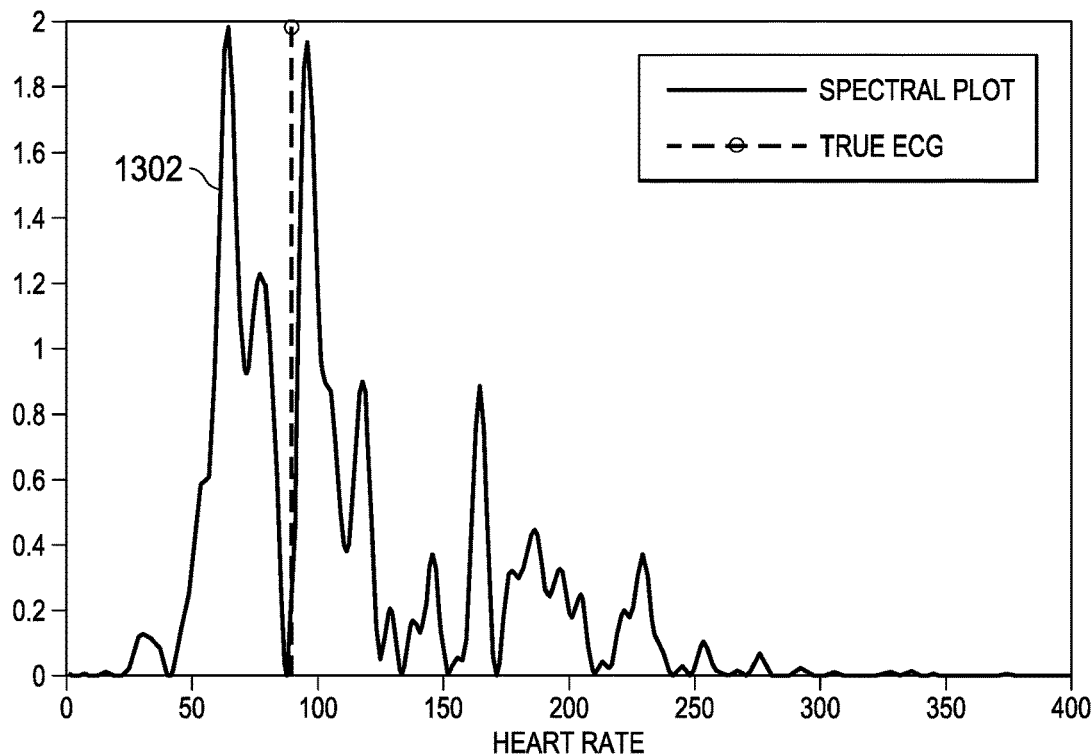
FIG. 13 is a diagram of a frequency spectrum of the PPG signal of FIG. 12 showing a peak value that does not represent the actual patient heart rate.
Figure 14:
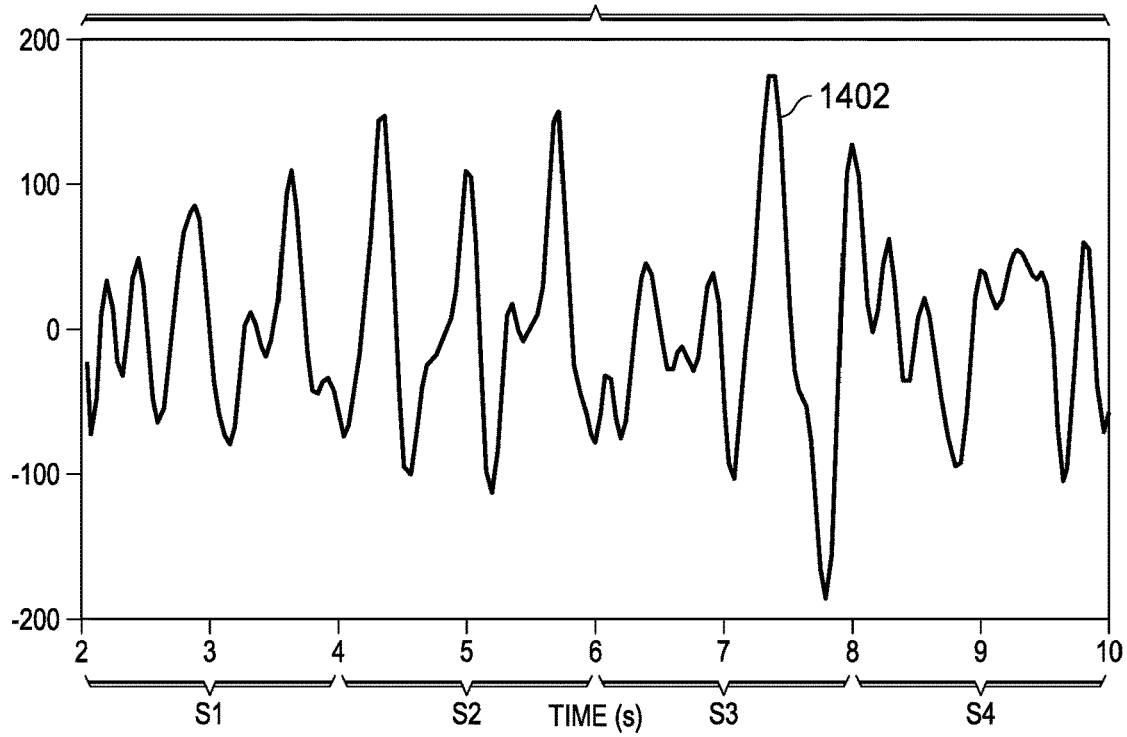
FIG. 14 is a diagram of a gain adjusted signal obtained by digital automatic gain adjustment of the PPG signal of FIG. 2.
Figure 15:
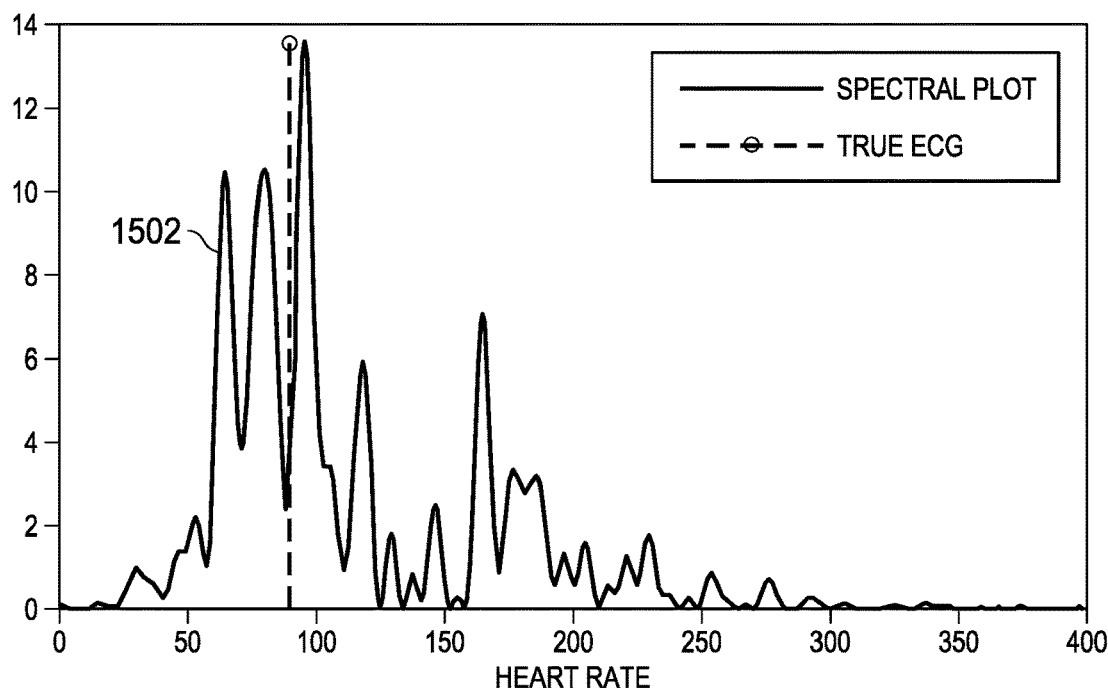
FIG. 15 is a diagram of a frequency spectrum of the gain adjusted signal of FIG. 14 showing a peak value near the actual patient heart rate.

FIGS. 12-15 illustrate another example, in which the accuracy of the HRE value 221 is improved by digital automatic gain control following motion compensation processing. A graph 1200 in FIG. 12 shows a waveform 1202 representing digital samples of a PPG signal obtained in an 8 second time window W1 that includes four segments S1-S4. In this example, after motion compensation processing, the data 1202 in the third segment S3 has a significantly larger amplitude than in the other segments S1, S2 and S4. A graph 1300 and FIG. 13 shows a frequency spectrum 1302 corresponding to the time domain PPG signal 1202 of FIG. 12. In this case, the highest peak in the spectrum 1302 is at a significantly lower frequency than the true (ECG-based) patient heart rate. A graph 1400 and FIG. 14 shows a gain adjusted PPG curve 1402 corresponding to gain adjusted samples (e.g., samples 217 in FIG. 2). The digital gain adjustment processing via the component 216 in this case has evened out the amplitude deviations between the segments S1-S4 compared to the original curve 1202 in FIG. 12. FIG. 15 provides a graph 1500 showing the resulting frequency spectrum curve 1502 corresponding to the gain adjusted time domain curve 1402. As seen in FIG. 15, the highest peak in the frequency spectrum 1502 is very close to the actual patient heart rate.

As seen in FIGS. 8, 9, 12 and 13 above, an FFT or other frequency domain analysis performed on a window W of the PPG samples 107 does not ensure accurate representation of the true patient heart rate based on the maximum peak in the spectrum, even if traditional motion compensation processing is performed prior to frequency domain analysis. In practice, motion compensation processing alone may not minimize the motion induced spectral peaks, and the maximum peak may not always correspond to the correct heart rate even after motion compensation processing. In particular, performing the heart rate estimate on a fairly large set of data in a relatively long time window W theoretically improves averaging in the frequency domain and thus promotes a more accurate heart rate estimate. However, FIGS.

8-15 show that high variance within segments of the time window W can lead to dominance in the FFT response by the segment of data with higher variance This variance discrepancy, in turn, can lead to inaccuracies in the estimated value of the patient heart rate.

The system 100 and the process 700 described above these problems by intelligent placement of the DAGC component 216 in the signal processing chain after motion compensation processing 214 and prior to FFT processing and heart rate tracking 218, 220. In particular, performing digital domain gain adjustment after any provided motion compensation processing, and before the FFT processing helps to ensure that the input to the FFT component 218 has an approximately constant variance, thus minimizing the distortion due to both movement of the sensor system 100 relative to the patient's body 120 (multiplicative motion artifacts) and additive motion artifacts associated with patient motion.

Figure 16:
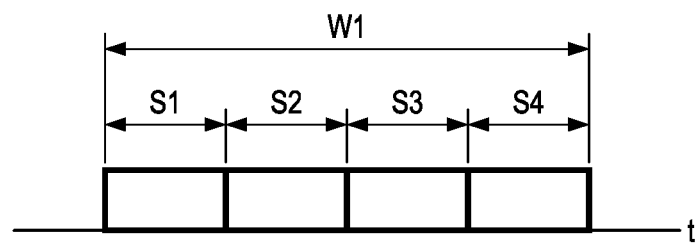
FIG. 16 is a diagram showing segments of a first time window for heat rate determination using the system of FIGS. 1 and 2.
Figure 17:
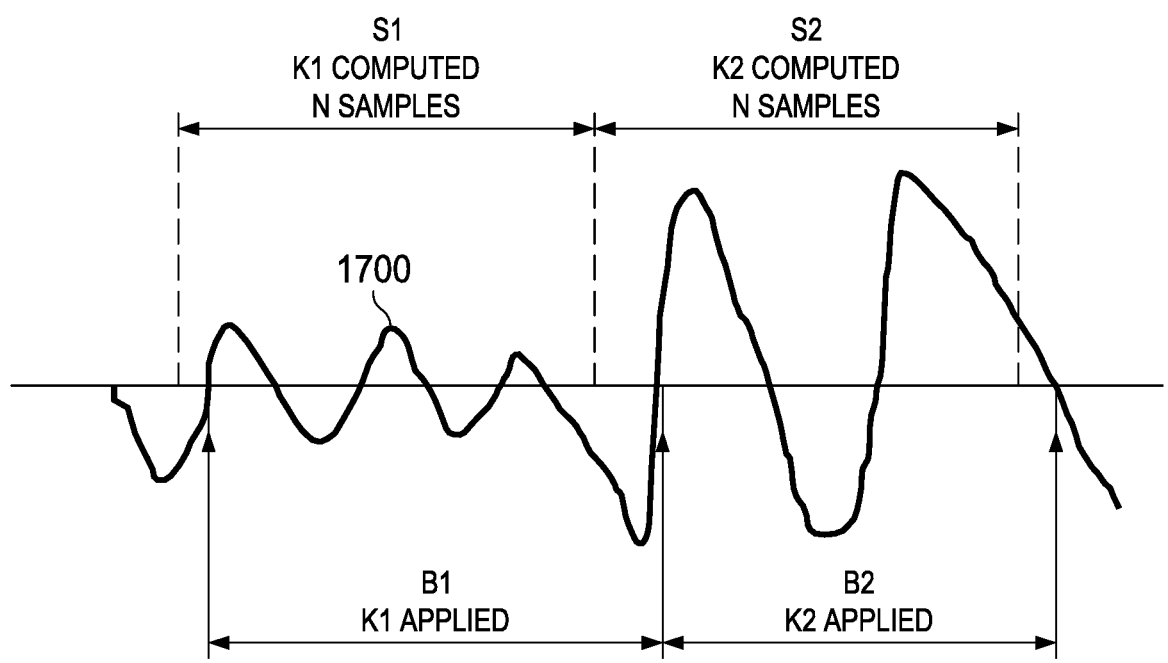
FIG. 17 is a diagram of a PPG signal showing two example segments and application of corresponding gain values to blocks beginning and ending at or adjacent to zero crossings of the PPG signal using the system of FIGS. 1 and 2.

Referring also to FIGS. 16 and 17, moreover, the digital automatic gain control processing in certain examples is performed based on zero crossings in order to avoid or mitigate introduction of high-frequency noise into the signal chain. FIG. 16 illustrates an example first time window W1 with four segments S1-S4 of generally equal length. FIG. 17 shows a portion of a motion compensated sample data curve 1700 for the first two segments S1 and S2, each including an integer number N samples. In this example, each of the segments S1 and S2 starts with a non-zero sample value. Applying a non-unity gain value K to either of these segments S1 or S2 would cause a discontinuity in the sample values, and thus introduce high-frequency noise into the gain adjustment process. This undesired additional frequency content, moreover, could further exacerbate inaccuracies in the frequency domain determination of the heart rate estimate value 221. In one example, the processor 108 implements the DAGC processing 216 on N samples associated with each segment S1-S4 of the motion compensated data samples 215 for a given time window W. The processor 108 initially computes the variance $\text{Var}_{ppgcomp}$ of the data as shown by the following equations (1):

$$\mu_{motioncomp} = \sum_{k=1}^{N} PPG_{motioncomp}(k) \quad (1)$$

$$\text{Var}_{ppgcomp} = \sum_{k=1}^{N} |PPG_{motioncomp}(k) - \mu_{motioncomp}|^2$$

In one example, the variance may be approximated according to the following equation (2), particularly where suitable front end filtering is performed in the AFE circuit 106 and/or by the digital filtering component 212:

$$\text{Var}_{ppgcomp} = \sum_{k=1}^{N} |PPG_{motioncomp}(k)|^2 \quad (2)$$

In this example, the processor 108 computes a scale factor $K_{scale}$ for each of the segments capital S1-S4 according to a predetermined target variance value targetVariance, using the following equation (3):

$$K_{scale} = \sqrt{\frac{targetVariance}{\text{Var}_{ppgcomp}}} \quad (3)$$

The processor 108 then multiplies the data values of a block B corresponding to the associated segment S by the scale factor $K_{scale}$ to generate the gain adjusted sample values 217. In some embodiments, the computed gain values can be applied using Boolean shifting left or right instead of a multiplicative scaling, for example, using the following equation (4) to determine a shift amount (number of bits) and a shift direction:

$$K_{shift} = \text{round}\left(0.5 \cdot \log_2\left(\frac{targetVariance}{\text{Var}_{ppgcomp}}\right)\right) \quad (4)$$

In this example, $K_{shift}$ is a power of 2 scale factor which corresponds to either binary left shifts of the motion compensated data 215 when $K_{shift}$ is positive, or to binary right shifts when $K_{shift}$ is negative.

As further shown in FIG. 17, the application of the computed gain values K, whether implemented through multiplication or the shifting, can be done based on blocks B that begin and end at samples including or adjacent to zero crossings in the sampled motion compensated data 215. The processor 108 in these examples determines block boundaries based on the zero crossing to the segment boundaries. In various implementations, the closest positive going zero crossings can be used, or the closest negative going zero crossings, or simply the closest zero crossings. As shown in FIG. 17, a first scaling factor or gain value K1 is computed for the first segment S1, and the scaling factor K–1 is applied to a corresponding block B1 that begins at the zero crossing closest to the beginning boundary of the segment S1, and the block B1 ends at the closest zero crossing after the end of the segment S1. The second illustrated block B2 begins at this same zero crossing, and ends at the closest zero crossing following the end of the second segment S1. This zero crossing based application of the computed gain values K prevents or mitigates sudden jumps or stepped changes in the data, and thus reduces or avoids generation of spectral distortion.

Referring again to FIG. 2, the system 100 in certain embodiments also employs feedback type gain adjustment of the AFE AGC circuit 202. In certain examples, the analog AGC circuit adjustment is also implemented at zero crossings of the analog PPG signal 105 in order to combat high frequency spectral distortion.

The above examples are merely illustrative of several possible embodiments of various aspects of the present disclosure, wherein equivalent alterations and/or modifications will occur to others skilled in the art upon reading and understanding this specification and the annexed drawings. Modifications are possible in the described embodiments, and other embodiments are possible, within the scope of the claims.

The following is claimed:
1. A heart rate monitor system comprising:
a light source configured to direct a first light signal;
an optical sensor configured to:
   detect a second light signal representing transmission or reflection of the first light signal; and
   generate an analog photoplethysmogram (PPG) signal representing the second light signal;

an analog-to-digital converter coupld to the optical sensor, the analog-to-digital converter configured to generate digital PPG sample values of the analog PPG signal for a time window, the time window comprising segments; and a circuit couple to the analog-to-digial converter, the circuit configured to:
- filter the digital PPG sample values to generate filtered values for the time window,
- perform motion compensation processing on the filtered values to generate motion compensated values for the time window,
- after the motion compensation processing, compute gain values to promote equalization of average power across the segments using the motion compensated values,
- apply the gain values to the motion compensated values to generate adjusted values in relation to the segments, and
- determine a heart rate estimate (HRE) value for the time window according to a frequency content of the adjusted values.

2. The heart rate monitor system of claim 1, wherein the circuit is configured to compute the frequency content of the adjusted values using a fast Fourier transform (FFT) algorithm to generate a frequency spectrum, and to determine the HRE value according to a discernible peak in the frequency spectrum.

3. The heart rate monitor system of claim 1, wherein the circuit is configured to:
- arrange the motion compensated values as a waveform along a time domain, in which the waveform comprises blocks respectively aligned with segments, and at least two of the blocks begin and end at a zero crossing of the waveform with respect to a zero reference value; and
- apply the gain values to the motion compensated values by applying the gain values to the respective ones of the blocks.

4. The heart rate monitor system of claim 1, wherein the analog PPG signal is a first analog PPG signal, the digital PPG sample values are first digital PPG sample values, the motion compensation processing is first motion compensation processing, the motion compensated calues are first motion compensated values, the gain values are first gain values, the adjusted valsue are first adjusted values, and the heart rate monitor system further comprises:
- a second light source configured to direct a third light signal;
- a second optical sensor configured to:
  - detect a fourth light signal representing transmission or reflection of the third light signal; and
  - generate a second analog PPG signal representing the fourth light signal;
- the analog-to-digital converter configured to generate second digital PPG sample values of the second analog PPG signal for the time window; and
- the circuit configured to:
  - filter the second digital PPG sample values to generate second filtered values for the time window,
  - perform second motion compensation processing on the second filtered values to generate second motion compensated values for the time window,
  - after the second motion compensation processing, compute second gain values to promote equalization of average power across the segments using the second motion compensated values,
  - apply the second gain values to the second motion compensated values to generate second adjusted values in relation to the segments,
  - combine the first adjusted values with the second adjusted values to generate combined adjusted values, and
  - determine the HRE value for the time window according to a frequency content of the combined adjusted values.

5. The heart rate monitor system of claim 1, wherein the analog PPG signal is a first analog PPG signal, the digital PPG sample values are first digital PPG sample values, the motion compensation processing is first motion compensation processing, the motion compensated values are first motion compensated values, the gain vlues are first gain values, and the heart rate monitor system further comprises:
- a second light source configured to direct a third light signal;
- a second optical sensor configured to:
  - detect a fourth light signal representing transmission or reflection of the third light signal; and
  - generate a second analog PPG signal representing the fourth light signal;
- the analog-to-digital converter configured to generate second digital PPG sample values of the second analog PPG signal for the time window; and
- the circuit configured to:
  - filter the second digital PPG sample values to generate second filtered values for the time window,
  - perform second motion compensation processing on the second filtered values to generate second motion compensated values for the time window,
  - combine the first motion compensated values with the second motion compensated values to generate combined motion compensated values,
  - after the first and second motion compensation processing, compute second gain values to promote equalization of average power across the segments using the combined motion compensated values,
  - apply the second gain values to the combined motion compensated to generate adjusted combined values in relation to the segments, and
  - determine the HRE value for the time window according to a frequency content of the adjusted combined values.

6. The heart rate monitor system of claim 1, wherein the circuit is configured to apply the gain values to the motion compensated values using binary bit shifting to generate the adjusted values.

7. The heart rate monitor system of claim 1, wherein the circuit is configured to selectively adjust a size of subsequent segments according to the HRE value for the time window.

8. The heart rate monitor system of claim 1, further comprising an analog gain controller coupled to the analog-to-digital converter, the circuit configured to selectively adjust the analog gain controller at least partially according to the gain values for the segments of the time window.

9. The heart rate monitor system of claim 8, wherein the analog PPG signal is arranged along a time domain as a waveform, and the circuit is configured to selectively adjust the analog gain controller in relation to a zero crossing of the waveform with respect to a zero reference value.

10. A method performed by a heart rate monitor system, the method comprising:
- receiving digital photoplethysmogram (PPG) sample values for a time window, the time window comprising segments, in which the digital PPG sample values are generated by analog-to-digital conversion of an analog PPG signal representing transmission or reflection of a light signal during the time window;

filtering the digital PPG sample values to generate filtered values for the time window;

performing motion compensation processing on the filtered values to generate motion compensated values for the time window;

after the motion compensation processing, computing gain values to promote equalization of average power across segments of the time window using the motion compensated values;

applying the gain values to the motion compensated values to generate adjusted values in relation to the segments; and determining a heart rate estimate (HRE) value for the time window according to a frequency content of the adjusted values.

11. The method of claim 10, further comprising:

arranging the motion compensated values as a waveform along a time domain, in which the waveform comprises blocks respectively aligned with the segments, and at least two of the blocks begin and end at a zero crossing of the waveform with respect to a zero reference value;

wherein apply the gain values to the motion compensated values by applying the gain values to the respective ones of the blocks.

12. The method of claim 10, further comprising applying the gain values to the motion compensated values using binary bit shifting to generate the adjusted values.

13. The method of claim 10, further comprising selectively adjusting a size of subsequent segments according to the HRE value for the time window.

14. The method of claim 10, wherein the analog-to-digital conversion comprises sampling the analog PPG signal with an analog gain controller, and selectively adjusting the analog gain controller at least partially according to the gain values for the segments of the time window.

15. The method of claim 14, wherein the analog PPG signal is arranged as a waveform along a time domain, and the method further comprises selectively adjusting the analog gain controller in relation to a zero crossing of the waveform with respect to a zero reference value.

16. A non-transitory computer readable medium storing instructions that are executable by a processor of heart rate monitor system to cause the heart rate monitor system to a perform a method comprising:

receiving digital photoplethysmogram (PPG) same values for a time window, the time window comprising segments, in which the digital PPG sample values are generated by analog-to-digital conversion of an analog PPG signal representing transmission or reflection of a light signal during the time window;

filtering the digital PPG same values to generate filtered values for the time window;

performing motion compensated processing on the filtered values to generate motion compensated values for the time window;

after the motion compensation processing, computing compute gain values to promote equalization of average power across the segments of the time window using the motion compensated values;

applying the gain values to the motion compensated values to generate adjusted values in relation to the segments; and determining a heart rate estimate (HRE) value for the time window according to a frequency content of the adjusted values.

17. The non-transitory computer readable medium of claim 16, wherein the methods comprises selectively adjusting a size of subsequent segments according to the HRE value for the time window.

18. The non-transitory computer readable medium of claim 16, wherein the method comprises applying the gain values to the motion compensated values using binary bit shifting to generate the adjusted values.

19. The non-transitory computer readable medium of claim 16, wherein the method comprises:

arranging the motion compensated values as a waveform along a time domain, in which the waveform comprises blocks respectively aligned with the segments, and at least two of the blocks begin and end at a zero crossing of the waveform with respect to a zero reference value;

wherein applying the gain values to the motion compensated values comprises applying the gain values to the respective ones of the blocks.

20. The non-transitory computer readable medium of claim 16, wherein the analog-to-digital conversion comprises sampling the analog PPG signal with an analog gain controller, and selectively adjusting the analog gain controller at least partially according to the gain values for the segments of the time window.

* * * * *